(12) United States Patent
Morf et al.

(10) Patent No.: US 10,973,488 B2
(45) Date of Patent: Apr. 13, 2021

(54) AUTOMATIC EXPOSURE CONTROL FOR X-RAY IMAGING

(71) Applicant: Varian Medical Systems International AG, Steinhausen (CH)

(72) Inventors: Daniel Morf, Buch am Irchel (CH); Reto Filiberti, Steinhausen (CH)

(73) Assignee: Varian Medical Systems International AG, Palo Alto, CA (US)

(*) Notice: Subject to any disclaimer, the term of this patent is extended or adjusted under 35 U.S.C. 154(b) by 78 days.

(21) Appl. No.: 16/392,790

(22) Filed: Apr. 24, 2019

(65) Prior Publication Data
US 2019/0269377 A1    Sep. 5, 2019

Related U.S. Application Data

(62) Division of application No. 14/858,961, filed on Sep. 18, 2015, now Pat. No. 10,285,661.

(51) Int. Cl.
*A61B 6/00* (2006.01)

(52) U.S. Cl.
CPC ........... *A61B 6/542* (2013.01); *A61B 6/4233* (2013.01); *A61B 6/469* (2013.01); *A61B 6/545* (2013.01)

(58) Field of Classification Search
None
See application file for complete search history.

(56) References Cited

U.S. PATENT DOCUMENTS

| | | | | |
|---|---|---|---|---|
| 6,535,576 B2* | 3/2003 | Vafi | ..................... | A61B 6/032 348/308 |
| 6,967,332 B2* | 11/2005 | Kobayashi | ............ | G01T 1/2018 250/370.09 |
| 9,091,770 B2* | 7/2015 | Okada | ............... | H01L 27/14663 |
| 9,383,458 B2* | 7/2016 | Okada | ..................... | G01T 1/247 |
| 9,835,732 B2* | 12/2017 | Fujiyoshi | .......... | H01L 27/14658 |
| 10,285,661 B2* | 5/2019 | Morf | ....................... | A61B 6/542 |
| 2003/0213914 A1* | 11/2003 | Kobayashi | ............... | H04N 5/32 250/370.09 |
| 2004/0101100 A1* | 5/2004 | Morii | ................ | H01L 27/14658 378/98.7 |
| 2011/0180717 A1* | 7/2011 | Okada | .................... | H04N 5/374 250/370.08 |
| 2013/0136233 A1* | 5/2013 | Okada | ............... | H01L 27/14658 378/62 |

(Continued)

*Primary Examiner* — Thomas R Artman
(74) *Attorney, Agent, or Firm* — Varian IP Legal

(57) ABSTRACT

In an x-ray imaging method, the acquisition of a signal image is split off into acquisition of two or more subimages or frames. The first subimage may be acquired with an exposure of a low dose followed by a readout cycle. The dose of the exposure for acquiring the first subimage can be chosen such that it is below the default dose for a particular anatomy. The first subimage may be used to calculate or estimate the parameters of exposure for acquiring a second or subsequent images subimage. The estimation may be such that the total dose received by the imager, in acquiring the first and second subimages, achieves an expected target value to provide an image of good quality. The first and second subimages can be combined to form the final image. A detector array supporting automatic exposure control (AEC) includes AEC pixels providing AEC signals. The AEC pixels are independently or individually addressable and/or readable.

15 Claims, 5 Drawing Sheets

(56) References Cited

U.S. PATENT DOCUMENTS

| | | | |
|---|---|---|---|
| 2015/0326810 A1* | 11/2015 | Okada | H04N 5/378 |
| | | | 378/98.2 |
| 2017/0079610 A1* | 3/2017 | Morf | A61B 6/469 |
| 2019/0269377 A1* | 9/2019 | Morf | A61B 6/545 |

* cited by examiner

AUTOMATIC EXPOSURE CONTROL FOR X-RAY IMAGING

CROSS REFERENCE TO RELATED APPLICATIONS

This application is a division of U.S. Ser. No. 14/858,961 filed Sep. 18, 2015 entitled "AUTOMATIC EXPOSURE CONTROL FOR X-RAY IMAGING," the disclosure of which is incorporated herein by reference in its entirety.

TECHNICAL FIELD

Embodiments of this disclosure relate generally to x-ray imaging systems and methods. In particular, various embodiments of automatic exposure control methods and imaging apparatuses and systems supporting automatic exposure control are described.

BACKGROUND

Automatic exposure control (AEC) is used in x-ray imaging for exposure management. The goal of AEC is to maintain image quality by delivering appropriate dose to the image detector while minimizing exposure on the patient. In conventional AEC methods, ion chambers or an array of semiconductor diodes are used to provide output signal in real time while the radiation dose is being delivered. Once a given threshold is reached, the exposure is terminated, typically via separate wiring to the x-ray source generator. The x-ray source generator typical has special dose integration electronics built in.

The conventional AEC methods require additional hardware such as AEC ion chambers or an array of semiconductor diodes and readout electronics etc. Very often, multiple AEC chambers are built in, and depending on the imaging setup one or more chambers are selected for exposure control. When in use, the AEC ion chambers are required to be placed at correct locations. Further, in cases where the AEC ion chambers are placed behind the image detector, low remaining radiation is available for the AEC ion chambers and thus low output signals because the image detector typically absorbs up to 70% of the radiation signal. If the AEC ion chambers are placed in front of the image detector when in use, some radiation which would otherwise contribute to image signals in the image detector would be attenuated.

It would be desirable to use the image detector itself to sense the exposure and provide AEC signals in real time without the use of additional AEC ion chambers. Flat panel image detectors are dose responsive and charge integrating devices. The signals that are captured by the image detector are only known after the exposure and the readout of the detector. Conventional flat panel detectors are generally designed to read out signals on a row-by-row or frame-by-frame basis, and not in real time.

Accordingly, there is a general need for an AEC method without the use of external AEC ion chambers or other measuring devices. There is a need for an imaging apparatus or system that incorporates an exposure dose integrating or measuring device or function for automatic exposure control.

SUMMARY

Certain embodiments of an automatic exposure control method and an imaging apparatus and system supporting automatic exposure control are set forth below. It should be understood that these embodiments are presented merely to provide the reader with a brief summary of certain forms the invention might take and that these embodiments are not intended to limit the scope of the invention. Indeed, the invention may encompass a variety of embodiments or aspects that may not be set forth below.

The disclosure provides an x-ray imaging method where the acquisition of a single image is split off into acquisition of two or more subimages or frames. The first subimage may be acquired with an exposure of a low dose followed by a readout cycle. The dose of the exposure for acquiring the first subimage can be chosen such that it is below the default dose or dose predetermined for a particular anatomy. The default dose, sometime also referred to as the template dose, is typically predetermined or known in advance depending on the anatomy being imaged. By way of example, the exposure dose for acquiring the first subimage may be one-third of the default dose in order to avoid over exposure in cases where the anatomy being imaged has far less attenuation than anticipated. Alternatively, the exposure dose for acquiring the first subimage can be chosen such that the dose received by the image detector is below an expected target value predetermined. The expected target value is a value for the image detector to generate images of good quality. The expected target value can be predetermined by the manufacturer or by the user, e.g., through intensive tests.

The first subimage may be used to calculate or estimate x-ray source parameters for producing exposure for acquiring a second subimage. The estimation may be such that the total dose received by the image detector, in acquiring the first and second subimages, achieves the expected target value, and thus provides an image of good quality. The first and second subimages may be combined to form the final image.

For dose estimation for acquiring the second subimage, the parameters of x-ray source (kV, mA, ms) in producing exposure for acquiring the first subimage, the signal received on the image detector, together with a lookup table may be used as the input for an estimation algorithm. As an alternative or additional source, a norm chamber value may be used for the dose estimation. A norm chamber is a dose measuring device built into an x-ray source for obtaining a dose reference for cone-beam CT image projections.

The disclosure further provides a flat panel detector array integrated or embedded with automatic exposure control functionality. The flat panel detector array can be integrated with a dose integrating or measuring device, which can turn off the x-ray beam sufficiently fast once the optimal dose on the detector is reached. For example, dose integrating/measuring pixels or AEC pixels may be distributed over the image detector array. The AEC pixels can be connected to fast readout electronics inside the image detector. The readout charges may be integrated in the detector electronics or in the image acquisition system. By way of example, every 10 mm×20 mm active detector area may contain an AEC pixel. Since only a small number of AEC pixels (in the above example, 1600 pixels for a 40 cm×40 cm detector array) are to be read, the readout can be sufficiently fast to terminate the exposure beam within a sufficiently short time once the optimal dose for an image of good quality is reached.

The readout mode of the AEC pixels can be changed to match different imaging readout modes of the flat panel detector e.g. for optimal dose setting, gain etc. The readout system of the AEC pixels can be configured such that different image areas can be selected based on the region of interest (ROI) via the image acquisition system.

In some alternative embodiments, predefined lines of pixels on a standard image detector array can be used to rapidly and in real-time measure the delivered dose during the x-ray on time. These predefined lines can be repeatedly readout and processed during the x-ray exposure. The dose of each line can be summed up. As soon as the desired dose is delivered or received, the system may stop the x-ray exposure and reads out the detector. In order to achieve a fast read-out time, only a few e.g. 20 lines or less can be readout. These lines can have faster readout timing than the typical line readout time because the accuracy requirement is much lower than for the standard imaging use case. The location of the lines may vary depending on the anatomy of the object being x-rayed. In some embodiments, only the lines inside a region of interest (ROI) might be readout and processed. Such an ROI may be predefined in anatomy templates or may be user selectable. It is also possible to define multiple ROIs and/or process only the interested part of a pixel-line.

The standard detector electronics can be used to readout the predefined lines, and the timing and the line sequencing can be adapted to that mode. The line readout timing can be drastically shortened such that only a fraction of the signal stored in the pixel is readout (e.g. 1 time constant). This may be sufficient to estimate the exposure level.

The dose of the monitoring-lines may be summed up line by line and added to the x-ray image later on. This way no dose (or image information) gets lost. Alternatively, the monitoring lines can be treated as defective lines and corrected by a pixel defect correction algorithm during image processing.

In some embodiments, individual pixels with dedicated readout and/or gate driver electronics can be used for dose monitoring instead of whole lines.

The disclosed features can be used in a variety of imaging systems, including x-ray imaging systems having a tight beam trigger interface with the x-ray generator. By way of example, the disclosed method can be implemented in multipurpose imaging systems used in radiation therapy imaging systems, or diagnostic imaging systems, which support multiple Imaging modalities such as live imaging, cine imaging, single images and cone beam CT imaging, and so on.

Other embodiments or aspects of the disclosure are described further herein.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of an automatic exposure control method, an imaging apparatus and system supporting automatic exposure control are described. It is to be understood that the disclosure is not limited to the particular embodiments described as such may, of course, vary. An aspect described in conjunction with a particular embodiment is not necessarily limited to that embodiment and can be practiced in any other embodiments. For instance, various embodiments are presented with an exemplary imaging modality. It will be appreciated that the disclosed methods can be implemented in a variety of imaging modalities including live imaging, cine imaging, single images and cone beam CT imaging etc. The features of disclosed methods are also particularly useful in radiation therapy imaging systems, which support multiple imaging modalities.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. In the following description, well known components or steps may not be described in detail in order to avoid unnecessarily obscuring the embodiments of the disclosure.

Embodiments of an automatic exposure control method, an image detection array, and an imaging system supporting automatic exposure control will now be described with reference to the figures. It should be noted that some figures are not necessarily drawn to scale. The figures are only intended to facilitate the description of specific embodiments, and are not intended as an exhaustive description or as a limitation on the scope of the disclosure.

Figure 1:
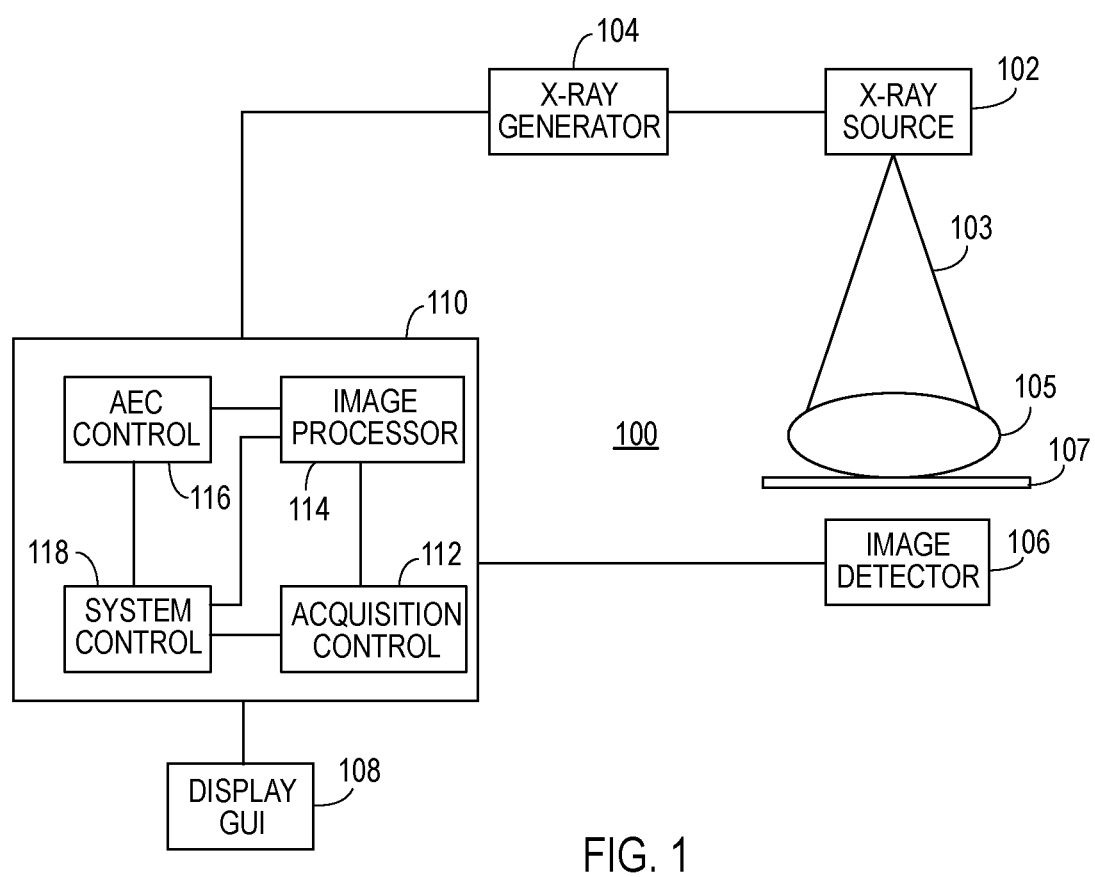
FIG. 1 depicts an exemplary imaging system according to embodiments of the disclosure.

FIG. 1 depicts an exemplary imaging system 100 provided with automatic exposure control functionality according to embodiments of the disclosure. As shown, the x-ray imaging system 100 may include an x-ray source 102, an x-ray generator 104, an image detector 106, an image acquisition system 110, and a user interface and display 108, interconnected substantially as shown. The x-ray source 102, upon excited by the x-ray generator 104, may emit an x-ray beam 103. The x-ray beam 103 may be directed to a subject 105 such as a patient supported on a patient support 107. A portion of the x-ray beam 103 may pass through the patient 105 and patient support 107, and impinge on the image detector 106. The image detector 106 may include an x-ray conversion material such as photoconductors that convert x-ray photons to electrical signals or scintillators that convert x-ray photons to visible light. The image detector 106 may further include a detector array that detects the electrical signals or converts visible light to electrical signals and detects the electrical signals.

The image acquisition system 110 may include an acquisition control 112, an image processor 114, an AEC control 116, and a system control 118, interconnected substantially as shown. The system control 118, by way of the user interface 108, may receive instructions from the user and govern the overall operation of the x-ray imaging system 100. The acquisition control 112 may include electronics for generating control signals for the image detector 106. The image processor 114 may process the signal data generated by the image detector 106 using suitable algorithms. The AEC control 116 may generate exposure control signals to the x-ray generator 104 based in part on the signals generated by the image detector 106, as will be described in greater detail below.

U.S. Pat. Nos. 5,970,115, 7,291,842, 7,816,651 and 8,552,386 disclose various embodiments of x-ray imaging apparatuses, systems, and components thereof, the disclosures of all of which are incorporated herein by reference in their entirety.

Figure 2:
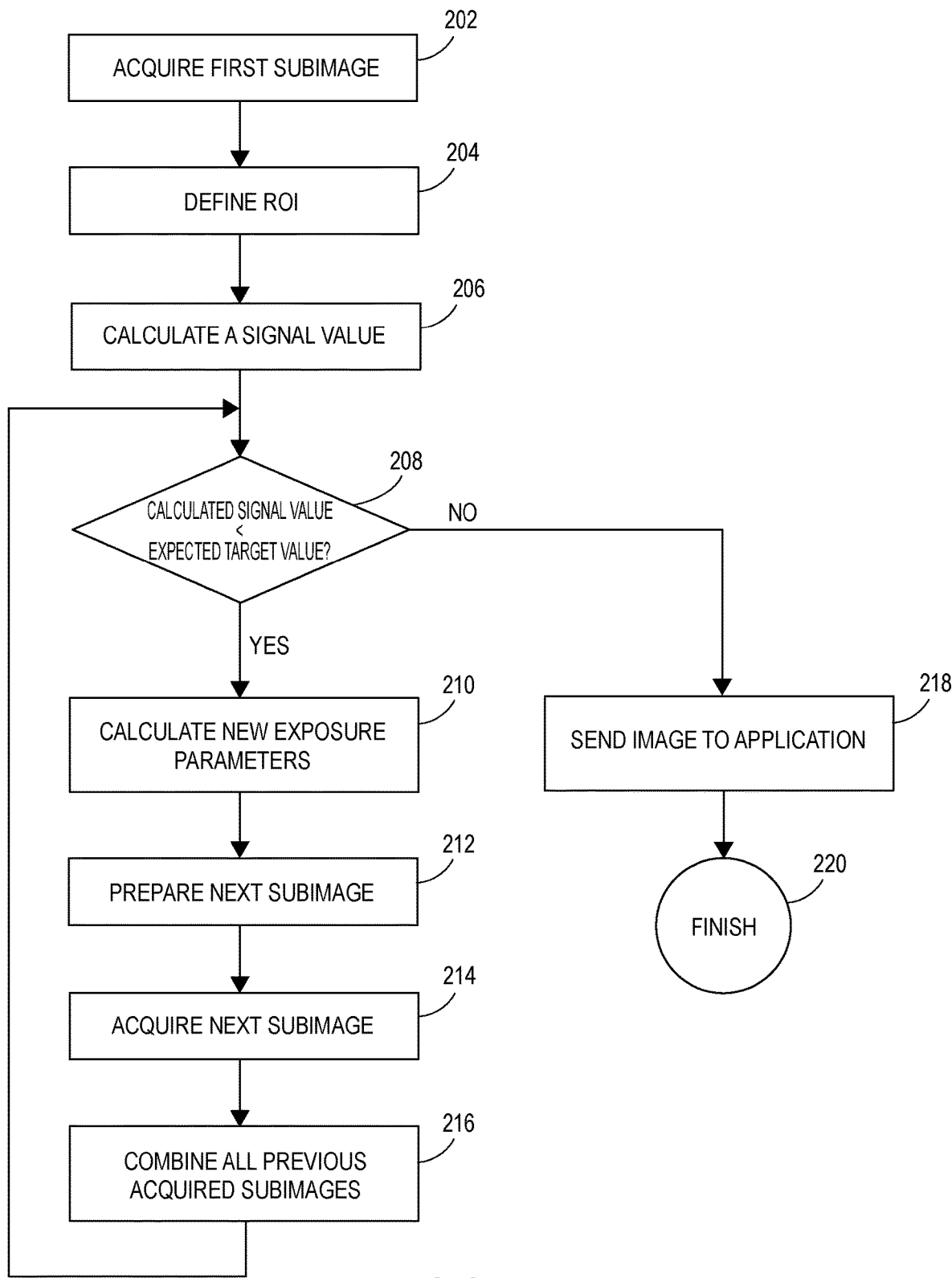
FIG. 2 is a flow chart illustrating exemplary steps of an image acquisition method according to embodiments of the disclosure.

Referring to FIG. 2, an x-ray imaging method with automatic exposure control will now be described. According to some embodiments, the acquisition of a single image of a subject, such as a body portion of a patient, an animal, a baggage, or an article of manufacture, is split off into acquisition of two or more subimages or frames. At step 202, a first subimage of a body portion may be acquired with a first exposure of x-ray produced by the x-ray source. The operation parameters of the x-ray source such as mA, ms, or kV can be set by the x-ray generator such that the first exposure produced by the x-ray source has a dose level lower than a default dose level predetermined for the body portion. For example, the body portion being imaged can be a patient's chest, abdomen, head, spine, or thorax, etc. taken in various directions such as antero-posterior (AP), postero-anterior (PA), lateral (L), etc. The default dose, sometime also referred to as the template dose, for various body portions or anatomies is typically predetermined or available from an "exposure table" known in the art. By way of example, if a chest AP is to be imaged, the user may look up an "exposure table" to find out the parameters of the x-ray source such as mA, ms, or kV for producing an exposure with the default dose. According to embodiments of the disclosure, the first subimage may be acquired with an exposure of a dose level lower than the default dose.

In some embodiments, the exposure dose for the first subimage may be two-third or lower of the default dose for the anatomy. In some embodiments, the exposure dose for the first subimage may be one half or lower of the default dose. In some embodiments, the exposure dose for the first subimage may be one-third or lower of the default dose. Indeed, depending on the anatomy to be imaged, the exposure dose for the first subimage may be one-fourth, one-fifth, or even one-tenth of the default dose in order to avoid overexposure in case the anatomy has far less attenuation than anticipated. In case the first subimage acquired does not provide sufficient information or signal value for analysis, a second subimage with e.g. 2, 3, 4, or 5 times or greater the dose level of the first subimage may be used. This second subimage may then be analyzed and the exposure parameters for a third subimage calculated. All three subimages may be combined to form the final image.

Alternatively, the exposure dose for the first subimage can be chosen such that the dose received by the image detector is below an expected target value, as will be described in greater detail below. For example, the exposure dose for the first subimage may be chosen such that the dose received by the image detector may be about two-third or lower of the expected target value, or one half or lower of the expected target value, or one-third or lower of the expected target value, or one-fourth, one-fifth, or even one-tenth of the expected target value in order to avoid overexposure in case the anatomy has far less attenuation than anticipated.

In some embodiments, the attenuation parameters of the body portion can be calculated and used in estimation of the first and/or subsequent exposure dose. The attenuation parameters of the body portion can be calculated from a 3D dataset acquired e.g. by a CT scan during the treatment planning session. In the simplest form e.g. only one type of material in the x-ray beam, the x-ray attenuation in the body portion can be expressed as Dose (Out)=Dose (In)×e^((−1)× attenuation parameter×thickness of the body portion).

Following the first exposure on the body portion with a dose level lower than the default dose, the signals captured by the image detector can be readout and processed, forming the first subimage of the body portion. The first subimage can be used to estimate the parameters of exposure for acquiring the second subimage, with the goal that the total dose received by the image detector, in acquiring the first and second or subsequent subimages, reaches the expected target value, and thus provides a final image of good quality as will be described in greater detail below.

Returning to FIG. 2, in order to estimate or calculate the parameters of x-ray source for producing exposure for acquiring the second subimage, the region of interest (ROI) on the first subimage is determined (step 204), and the signal value of the ROI on the first subimage is calculated (step 206). It is also conceivable to calculate the parameters using multiple ROIs. As used herein, the term "region of interest" or "ROI" refers to content in a body portion, including but not limited to tumor, malignant tissue, healthy tissue, bone, organ, or any other content, that has a signal value on a subimage.

The region of interest on the first subimage may be a particular anatomy, organ, tissue, tumor, or other malignant lesions etc. However, the first subimage may also contain other regions, such as air, bones, implants (metals) etc. that are of no or less interest. In order to optimize the image quality on the region of interest, the signal value of the ROI on the first subimage should be calculated and taken into account in estimating the exposure dose for the second or subsequent subimage, whereas the signal value of other regions such as air or implants should be excluded in calculation. Inclusion of signal values of other regions in calculation would cause the ROI value in estimating the exposure level for the subsequent subimages too high or too low. Alternatively, algorithms may be implemented to account for the above mentioned structures.

The region of interest on the first subimage for dose estimation can be defined by the user using an anatomy template. Alternatively, the ROI can be selected automatically using an algorithm based on the content of the first subimage. For example, an algorithm can search for the desired image content by e.g. excluding air or implants and determine the ROI based on the content of the first subimage. An exemplary algorithm may use histogram to find relevant pixel values, excluding very low pixel value (e.g. near 0 value) or very high pixel value (typically for air), and take the average or median value of relevant pixels. U.S. Pat. No. 7,599,539 to the present assignee describes various methods for detecting, identifying, or highlighting regions of interest in digital images, the disclosure of all of which is incorporated herein by reference in its entirety.

More sophisticated algorithms, e.g. Varian Smart Segmentation® software available from Varian Medical Systems, Inc. in Palo Alto, Calif., can be used to automatically segment certain regions or organs in the image. The knowledge-based automated contouring or segmentation provides information from the segmented regions, which can be further processed in the automatic exposure control algorithm to provide exposure parameters for acquiring subsequent subimages, to be combined with the first subimage to form a final image with an optimal image quality, as will be described in greater detail below. For example, the ROI and the signal value of the ROI on the first subimage can be automatically determined using the Smart Segmentation® software and the information can be imported to the AEC algorithm for calculation of the exposure parameters for acquiring subsequent subimages.

Returning to FIG. 2, the parameters of the x-ray source for producing a second exposure for acquiring a second subimage of the body portion may be calculated based on the signal value of the ROI on the first subimage (step 210). The objective of the calculation is that the calculated parameters provide a second exposure with a dose level such that a signal value of the ROI on the second subimage is achieved and the sum of the signal value of the ROI on the second subimage and the signal value of the ROI on the first subimage is no less than an expected or predetermined target signal value.

The expected target value may be a value for the image detector to generate an image of good quality. The expected target value can be predetermined by the manufacturer of the image detector. For example, an expected target value may be determined or obtained through intensive tests on an image detector. The expected target value may also be determined by the user by modifying the default value provided by the manufacturer.

The calculation of the parameters for producing exposure for acquiring the second or subsequent subimages can be carried out using a dose estimation algorithm. The input for the dose estimation algorithm may include the parameters in producing the first exposure (kV, mA, ms) for acquiring the first subimage, the signal value received on the image detector for the first subimage, and/or a lookup exposure table etc. As an alternative or additional source, a norm chamber value may be used for the dose estimation.

Any suitable dose estimation algorithms can be used to calculate the exposure parameters for the second or subsequent subimages. In principle, the response of an image detector or the signal value is linear with the radiation dose received. Therefore, for example, if the signal value of the ROI on the first subimage is determined as e.g. 20% of the expected target value, then the signal value for the ROI on the second subimage can be 4 times higher (+80%). The dose of an exposure produced by an x-ray source is generally linear with the parameters mA and ms of the x-ray source. Therefore, by determining a desired signal value of the ROI on a second subimage, the exposure parameters mA and ms for acquiring the second subimage can be readily calculated and selected.

The dose of an exposure produced by an x-ray source is generally nonlinear with the parameter kV of the x-ray source. In case that it is desirable to adjust the kV parameter in order to achieve the expected target dose, a look-up table can be used in the estimation. For example, in a multi-energy x-ray imaging, the first subimage may be acquired using low kV and half the default dose. The dose for the second subimage can then be estimated based on the first subimage, but with the condition that the second subimage uses a higher or lower kV value. The two subimages can then be processed using algorithms known in the art.

Returning to FIG. 2, the calculated exposure parameters (mA, ms, and/or kV) may be sent to the x-ray generator for preparation of acquiring the second or subsequent subimage (step 212). An exposure of x-ray may be emitted by the x-ray source under the new parameters, and a second subimage is acquired (step 214). A single image of the body portion may be formed by combining the first and second subimages, e.g., on a pixel by pixel basis. By combining the two subimages, all doses from the first and second exposures are used in forming the image of the body portion and no dose is wasted.

To speed up the combined exposure, the readout parameters of the image detector can be changed between the acquisitions of the subimages. For example, a faster readout mode with a lower resolution and/or higher amplification may be used for the acquisition of the first subimage. A readout mode with a higher resolution and/or lower gain may be used for the subsequent subimage(s).

In some embodiments, the signal value of the ROI on the acquired second subimage is determined, and the signal values of the ROI on the acquired second subimage and the acquired first subimage are combined (step 216). The combined signal values are then compared with the expected target signal value, as shown at step 208. If the combined signal values of the ROI on the acquired second and first subimages are no less than the expected target signal value, then the acquired first and second subimages are combined pixel-by-pixel to form an image of the body portion. The image is sent to application (step 210) and the process is finished (step 220) If the combined signal values of the ROI on the acquired second and first subimages are less than the expected target signal value, then parameters for producing exposure for acquiring a third subimage are calculated. The input and process for calculating parameters for acquiring the third subimage are similar to those for calculating parameters for acquiring the second subimage, with an exception that the combined signal values of the ROI on the acquired second and first subimages are used in the calculation for the third subimage. The goal for the calculation is that the calculated parameters for the third exposure provide a dose level such that the sum of the signal values of the ROI on the third subimage and the combined signal values of the ROI on the acquired second and first subimages is no less than the predetermined target signal value. A third subimage may then be acquired using the calculated exposure parameters, and an image of the body portion can be formed by combining all subimages on a pixel-by-pixel basis. These steps can be repeated until the combined signal value of the ROI on all subimages is no less than the expected target value.

Figure 3:
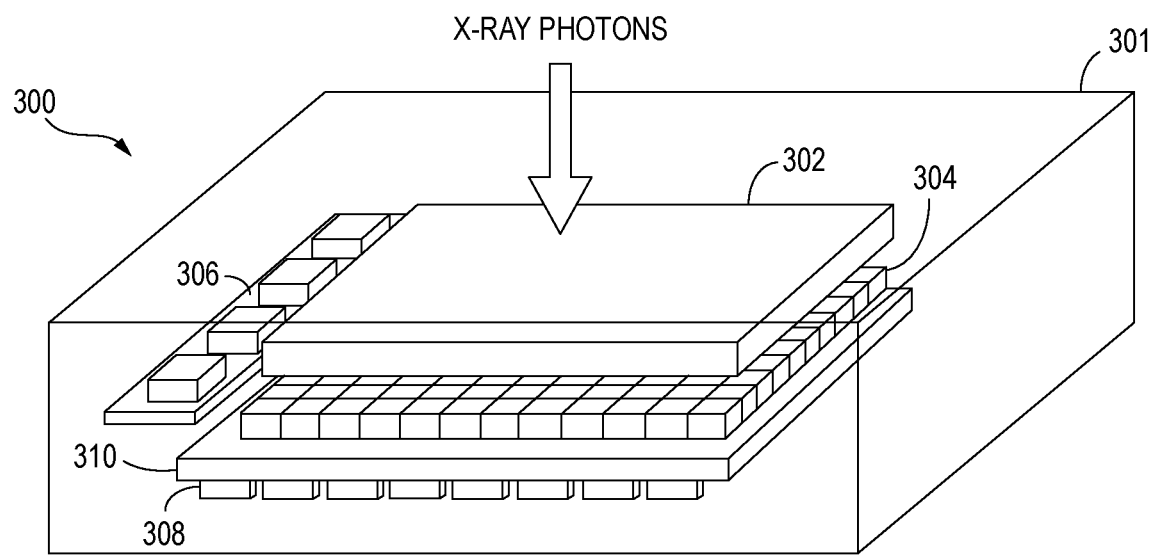
FIG. 3 depicts an exemplary x-ray image detector according to embodiments of the disclosure.
Figure 4:
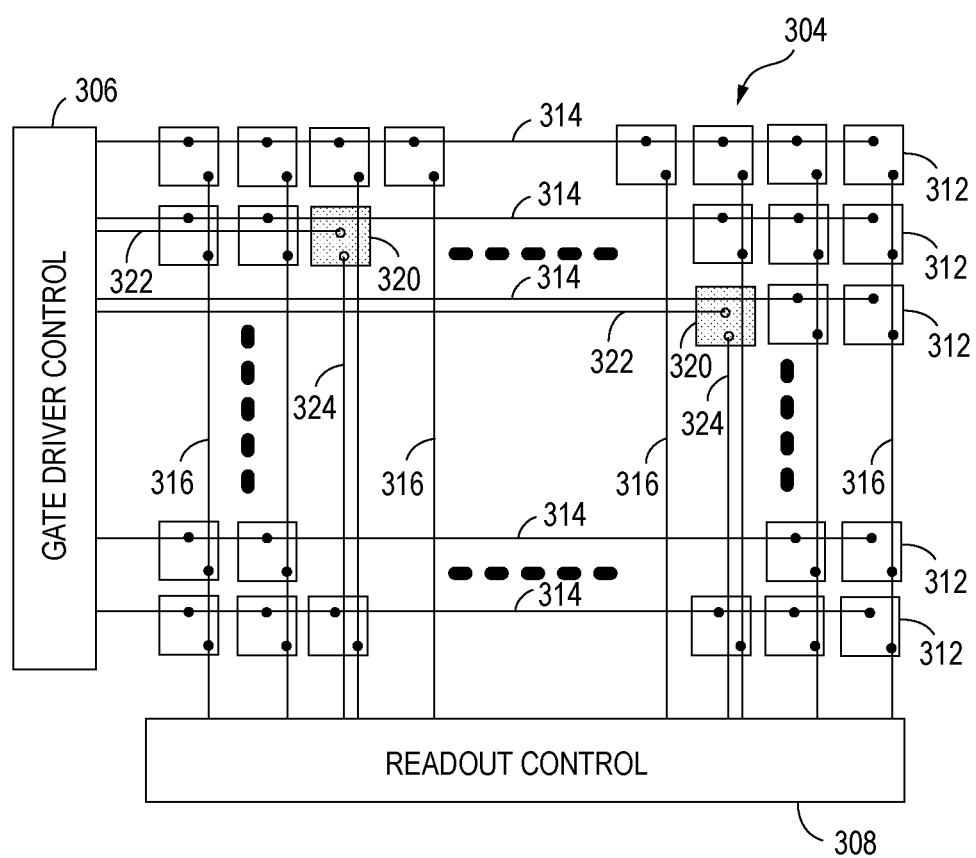
FIG. 4 depicts an exemplary detector array supporting automatic exposure control according to embodiments of the disclosure.
Figure 5:
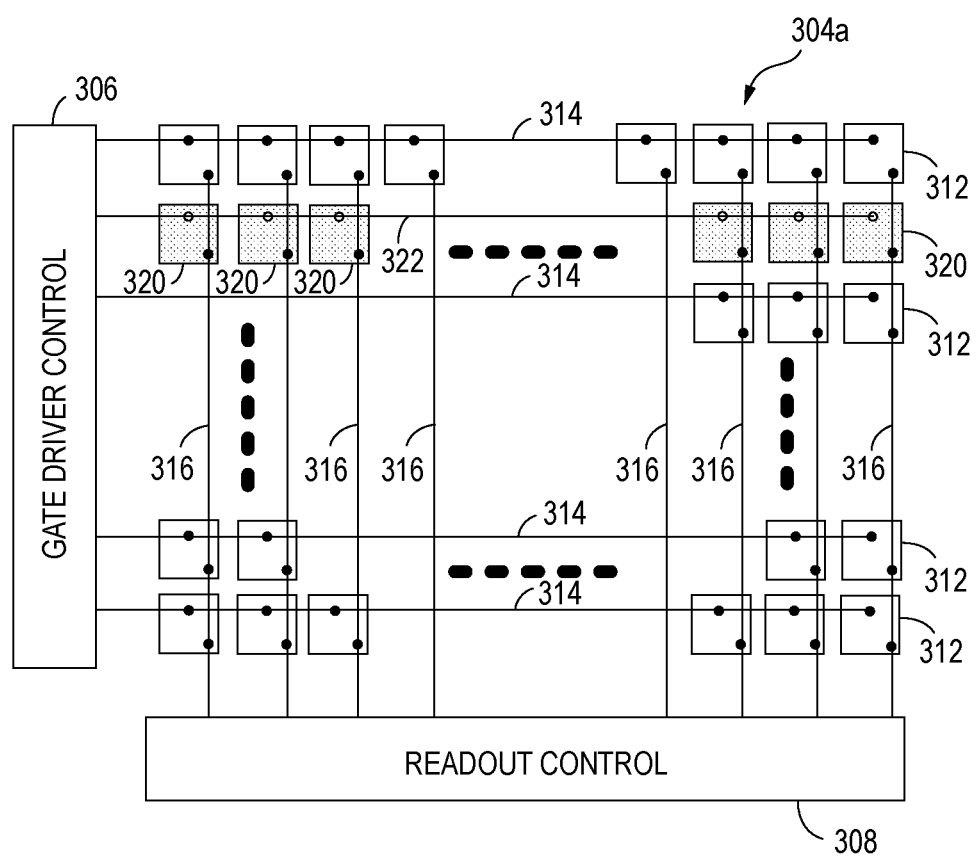
FIG. 5 depicts another exemplary detector array supporting automatic exposure control according to embodiments of the disclosure.

Referring now to FIGS. 3-5, an imaging apparatus supporting automatic exposure control will be described. FIG. 3 is a schematic representation of a flat panel image detector 300 according to some embodiments of the disclosure. As shown, the image detector 300 may include a radiation conversion layer 302, a detector array 304, a driver control assembly 306, and a readout control assembly 308. The radiation conversion layer 302 may be configured to convert x-ray photons to visible light. The detector array 304 may convert visible light to electrical signals and detect the electrical signals. The driver control assembly 306 provides control signals for addressing the signal data generated by the detector array 304. The readout control assembly 308 provides control signals for reading out the signal data. In the exemplary embodiment shown in FIG. 3, the detector array 304 and the readout control assembly 308 may be mounted on opposing sides of a base plate 310. For example, the electronics of readout control assembly 308 may be placed beneath the detector array 304 to minimize the lateral size of the image detector 300. The electronics of the driver control assembly 306 can also be placed beneath the detector array 304 or at a side or sides of the detector array 304. A housing 301 may enclose the radiation conversion layer 302, the detector array 304, the driver control assembly 306, and the readout control assembly 308 inside.

The conversion layer 302 may include a scintillator material which can generate visible light photons in response to x-ray radiation. As such, the detector array 304 may include photosensitive elements which can generate electrical signals in response to the light photons generated by the scintillator material. Suitable scintillator materials include gadolinium oxisulfide ($Gd_2O_2S$:Tb), cadmium tungstate ($CdWO_4$), bismuth germanate ($Bi_4Ge_3O_{12}$ or BGO), cesium iodide (CsI), cesium iodide thallium (CsI:TI), Thallium doped Sodium Iodide NaI(TI) or any combination thereof. Suitable photosensitive element may include a photodiode, a photogate, or phototransistors etc. In alternative embodiments, the conversion layer 302 may include a photoconductor material which can convert x-ray photons to electrical charges (electron-hole pairs) directly. As such, the detector array 304 may include electrodes at either side of the photoconductor material to collect the electrical charges generated by the photoconductor material. Suitable photoconductor materials include and are not limited to mercuric iodide ($HgI_2$), lead iodide ($PbI_2$), bismuth iodide ($BiI_3$), cadmium zinc telluride (CdZnTe), amorphous selenium (a-Se), etc.

FIG. 4 depicts an exemplary flat panel detector array 304 according to some embodiments of the disclosure. The detector array 304 shown in FIG. 4 is provided with automatic exposure control functionality. As shown, the exemplary detector array 304 may include a large number e.g. hundreds of thousands or millions of detector pixels 312. The large number of detector pixels 312 may be arranged in a plurality of rows and a plurality of columns forming an active detector area. In some specific embodiments, each detector pixel 312 may include an addressable photosensitive element such as a photodiode and a switching transistor such as a TFT or CMOS transistor.

The detector array 304 may further include a plurality of address lines 314 and a plurality of data lines 316. Each of the plurality of address lines 314 may connect a plurality of detector pixels 312 in a row to a driver control assembly 306. Each of the plurality of data lines 316 may connect a plurality of detector pixels 312 in a column to a readout control assembly 308. The driver control assembly 306 provides control signals for accessing a selected row of pixels 304. The readout control assembly 308 provides control signals for reading out the signals from the pixels 312. By way of example, when it is desired to capture image signals from the detector array 304, a control signal from the driver control assembly 306 drives the gates of switching elements e.g. TFTs in a selected row of pixels 312, and the signals stored in the selected row of pixels 312 are readout by the readout control assembly 308. The signals from the selected pixels 312 may be buffered, amplified, and converted by analog-to digital converters (ADCs) using electronics and techniques known in the art. The resulting digitized data signals can be then multiplexed, buffered, and transmitted to an image processor for further processing.

Still referring to FIG. 4, the detector array 304 may include a number of AEC pixels 320 which provides signals for automatic exposure control. In FIG. 4, the AEC pixels 320 are grayed and the non-AEC pixels are indicated as having white background for clarity of illustration. Two AEC pixels are shown in FIG. 4 for illustration. It will be appreciated that the disclosure is not so limited and the number of AEC pixels can vary based on the application and size of the detector array. By way of example, the flat panel detector array 304 may include about 0.001 to about 0.2 percent of AEC pixels, or about 0.1 to about 1 percent of AEC pixels. In a specific embodiment, the flat panel detector array 304 may include from 30 to 30,000 AEC pixels out of a total of 3 million detector pixels. It should be noted that the specific values provided herein are for illustration purpose only and not intended to limit the scope of the claims of the disclosure.

The AEC pixels 320 may be distributed over the detector array 304 in any suitable arrangement. For example, every active detector area of about 1 mm×1 mm to about 50 mm×50 mm may contain an AEC pixel, or every active detector area of about 2 mm×2 mm to about 20 mm×20 mm may contain an AEC pixel, or every active detector area of about 5 mm×5 mm to about 20 mm×20 mm may contain an AEC pixel, or every active detector area of about 10 mm×10 mm to about 20 mm×20 mm may contain an AEC pixel, or every active detector area of about 15 mm×15 mm to about 20 mm×20 mm may contain an AEC pixel. In another specific example, 10,000 to 20,000 AEC pixels, or 5,000 to 10,000 AEC pixels, or 2,500 to 5,000 AEC pixels, or 250 to 2,500 AEC pixels, or 10 to 750 AEC pixels may be distributed over a 40 cm×40 cm active detector area, which may include a total of 3 million detector pixels. It should be noted that the specific values provided herein are for illustration purpose only and not intended to limit the scope of the claims of the disclosure.

The AEC pixels 320 may have a structure or size substantially same as the non-AEC pixels 312. Alternatively, the AEC pixels 320 may have a structure or size different from a structure or size of non-AEC pixels 312.

Still referring to FIG. 4, each of the AEC pixels 320 may be independently or individually addressable and/or readable. As shown, each of the AEC pixels 320 may be connected to the driver control assembly 306 by a dedicated address line 322 and to the readout control assembly 308 by a dedicated data line 324. Therefore, each of the AEC pixels 320 may be independently or individually accessible by the driver control assembly 306 and the readout control assembly 308. Alternatively, each of the AEC pixels 320 may be individually addressed and/or read out by the driver control assembly 306 and/or the readout control assembly 308, independent of the addressing and readout of the remaining non-AEC pixels 312 in the same row as the addressed AEC pixel 320. In some embodiments, the non-AEC pixels 312 in a row may be connected to the driver control assembly 306 by a single address line 314. The non-AEC pixels 312 in a column may be connected to the readout control assembly 308 by a single data line 316. In some other embodiments, the AEC pixels may be connected to dedicated driver and readout electronic circuits.

In conventional detector arrays, all pixels in a row are connected to an array driver control circuit via a same address line, and all pixels in a column are connected to a readout control circuit via a same data line. In operation of the conventional detector arrays, the control signal from the driver control circuit for a row of pixels is asserted on a single address line for a predetermined period of time or "line time." During assertion of the control signal, the signal from each pixel in the selected row is transmitted via column data lines to the readout control circuit where the signals on each data line are received and buffered by a corresponding charge sensitive amplifier. Hence, an entire row of image data is captured in a "line time" period. With each subsequent line time period, a subsequent row of image data is captured. At the end of a "frame time" period, the entire image is captured. In this manner, the pixels contained in the entire active detection area are read out, row-by-row, each row in a line time period. Because the signals are readout on a row-by-row basis, it is problematic or impossible to use conventional detector arrays to provide automatic exposure control in real time using conventional methods.

In accordance with certain embodiments of the disclosure, a number of AEC pixels 320 are distributed over the detector array 304 as shown in FIG. 4. Each of the AEC pixels 320 can be independently or individually addressed by the driver control assembly 306 via a dedicated address line 322, and/or independently or individually read out by the readout control assembly 308 via a dedicated data line 324. Therefore, signals from the AEC pixels 320 can be readout continuously, integrated, and provided to the x-ray generator for exposure control. Once the integrated signals measured by the AEC pixels 320 indicate that a desired dose level is reached, the system may generate a control signal to terminate the exposure beam. Since only a limited or small number of AEC pixels are to be read, the readout of the AEC signals 320 can be sufficiently fast. The readout electronics for the AEC pixels 320 can be designed and constructed for fast readout because the requirement for high resolution is low. The readout charges may be integrated in the image detector electronics or in the image acquisition electronics.

Since the AEC pixels 320 distributed over the detector array 304 can be individually selected and/or read, the area of the detector array 304 used for exposure control can be defined corresponding to the size, shape, or number of the region of interest in a subject being imaged. The readout system for the AEC pixels 320, including the driver control 306 and readout control 308 electronics, can be configured or constructed to allow the user to individually select the AEC pixels 320 such that the selected AEC pixels define an exposure control area with a shape and size generally corresponding to the region of interest (ROI) in the subject being imaged.

FIG. 5 depicts an exemplary flat panel detector array 304A provided with automatic exposure control functionality according to some embodiments of the disclosure. The detector array 304A shown in FIG. 5 is similar to the detector array 304 shown in FIG. 4 in many aspects. For example, the detector array 304A may include a large number e.g. hundreds of thousands or millions of pixels 312, 320 arranged in a plurality of rows and a plurality of columns forming an active detector area. The detector array 304A may include a plurality of address lines 314, 322 and a plurality of data lines 316. Each of the plurality of address lines 314, 322 may connect a plurality of pixels 312, 320 in a row to the driver control assembly 306. Each of the plurality of data lines 316 may connect a plurality of pixels 312 in a column to the readout control assembly 308. The detector array 304A may also include a number of AEC pixels 320 which provides signals for automatic exposure control. In FIG. 5, the AEC pixels 320 are grayed and the non-AEC pixels 312 are indicated as having white background for illustration with clarity. In some embodiments, the AEC pixels may be standard pixels that are selected to be used for the AEC signal calculation. Apart from firmware changes, there can be no special detector design required.

In comparison with FIG. 4, the AEC pixels 320 in the detector array 304A shown in FIG. 5 may be arranged in a row. The AEC pixels 320 may make up entire one or more rows of the plurality of rows of the detector array 304. The row of AEC pixels 320 may be connected to the drive control assembly 306 via a dedicated address line 322. For clarity of illustration and description, only one row of AEC pixels is shown in FIG. 5. It will be appreciated that the disclosure is not so limited and the number of rows consisting of AEC pixels may vary based on the application and size of the detector array 304A. By way of example, the detector array 304A may include 1-200 rows, or 1-30 rows, or 1-20 rows, or 1-10 rows, or 10-20 rows, or 6-20 rows, or 6-10 rows of AEC pixels.

The row or rows of AEC pixels 320 may be specially designed for automatic exposure control in fabrication of the detector array 304A. Alternatively, the row or rows of AEC pixels 320 may be predefined by the user in a standard detector array for automatic exposure control. The rows of AEC pixels 320 can be used to rapidly and in real-time measure the delivered dose on the detector array 304A during the x-ray on time. These dedicated or predefined rows can be repeatedly readout and processed during the x-ray exposure, and the dose can be summed up. The readout electronics, including the drive control assembly 306 and/or readout control assembly 308, can be designed and constructed such that the rows of AEC pixels have faster readout timing than the typical readout time for the rows of non-AEC pixels since the resolution accuracy requirement for the rows of AEC pixels is much lower than that for the standard imaging use case. The location of the AEC rows may vary depending on the anatomy of the object being x-rayed. In some embodiment, only the rows of AEC pixels inside the region of interest may be readout and processed. The region of interest may be predefined in the anatomy template or may be user selectable. It is also possible to define multiple ROIs and/or process only in the interested part of an AEC pixel line.

As soon as a desired dose received by the detector array 304A is reached, as indicated by the integrated signals measured by the AEC pixel rows, the system may generate a control signal to terminate the x-ray exposures. The image signals in the detector array 304A may then be read out using a standard readout scheme.

In processing the image signals, the dose received by the monitoring rows of AEC pixels may be summed up and added to the image signals. This way no dose (or image information) would be lost. Alternatively, the monitoring AEC rows may be treated as defective lines and corrected using a pixel defect correction algorithm.

In some embodiment, the standard detector electronics can be used to readout the predefined AEC lines, and the timing and the line sequencing can be adapted to that mode. The line readout timing can be drastically shortened such that only a fraction of the signal stored in the pixel is readout (e.g. 1 time constant). This may be sufficient to estimate the exposure level.

An automatic exposure control method and an image detection array supporting automatic exposure control have been described. Those skilled in the art will appreciate that various other modifications may be made within the spirit and scope of the invention. All these or other variations and modifications are contemplated by the inventors and within the scope of the invention.

What is claimed is:

1. An apparatus comprising a detector array supporting automatic exposure control (AEC), the detector array comprising:
   a plurality of detector pixels generating electrical signals in response to x-ray photons, the plurality of detector pixels being arranged in a plurality of rows and a plurality of columns defining an active detector area;
   a plurality of address lines providing control signals to address the plurality of detector pixels; and
   a plurality of data lines reading out the plurality of detector pixels; wherein
      the detector pixels comprise AEC pixels, the AEC pixels making up one or more entire rows of the plurality of rows of detector pixels.

2. The apparatus of claim 1,
   wherein
      each of one or more rows of the AEC pixels is independently addressable by one of the plurality of address lines and/or independently readable by one of the plurality of data lines.

3. The apparatus of claim 1, wherein 1 to 30,000 AEC pixels are distributed in the active detector area of about 40 cm×40 cm.

4. The apparatus of claim 1, wherein about 0.001 to about 1 percent of the detector pixels are AEC pixels.

5. The apparatus of claim 1, wherein the AEC pixels have a structure or size substantially same as a structure or size of non-AEC pixels.

6. The apparatus of claim 1, wherein the AEC pixels have a structure or size substantially different from a structure or size of non-AEC pixels.

7. The apparatus of claim 1, further comprising an addressing circuitry dedicated to addressing the AEC pixels and a readout circuitry dedicated to reading out the AEC pixels.

8. The apparatus of claim 1, wherein the AEC pixels make up 1-200 entire rows of the plurality of rows of the detector pixels.

9. The apparatus of claim 1, wherein:
the one or more rows of AEC pixels are addressed and/or read out by a first electric circuitry, and
the remaining rows of the detector pixels are addressed and/or read out by a second electric circuitry different from the first electric circuitry.

10. The apparatus of claim 9, wherein the first electric circuitry addresses and/or reads out signals from the one or more rows of AEC pixels faster than the second electric circuitry that addresses and/or reads out signals from remaining rows of the detector pixels.

11. The apparatus of claim 1, further comprising an addressing circuitry addressing both the one or more rows of AEC pixels and the remaining rows of the detector pixels and a readout circuitry reading out both the one or more rows of AEC pixels and the remaining rows of the detector pixels.

12. A radiation method, comprising:
positioning a subject between an x-ray source and an image detector, wherein the image detector comprising a detector array comprising:
a plurality of detector pixels generating electrical signals in response to x-ray photons, the plurality of detector pixels being arranged in a plurality of rows and a plurality of columns defining an active detector area;
a plurality of address lines providing control signals to address the plurality of detector pixels; and
a plurality of data lines reading out the plurality of detector pixels;
emitting an exposure of x-ray from the x-ray source to the subject;
reading out signals from selected detector pixels while the exposure of x-ray is on, wherein the selected detector pixels make up one or more entire rows of the detector;
integrating the signals from the selected detector pixels;
terminating the exposure of x-ray when the integrated signals reach an expected target value.

13. The method of claim 12, wherein the selected detector pixels collectively approximate a shape of a region of interest.

14. The method of claim 13, wherein the selected detector pixels are independently addressable by a dedicated addressing circuitry and independently readable by a dedicated readout circuitry.

15. The method of claim 12, wherein the selected detector pixels are independently addressable by a dedicated addressing circuitry and independently readable by a dedicated readout circuitry.

* * * * *